United States Patent
Glukhovsky et al.

(10) Patent No.: US 7,118,529 B2
(45) Date of Patent: Oct. 10, 2006

(54) METHOD AND APPARATUS FOR TRANSMITTING NON-IMAGE INFORMATION VIA AN IMAGE SENSOR IN AN IN VIVO IMAGING SYSTEM

(75) Inventors: Arkady Glukhovsky, Santa Clarita, CA (US); Zvika Gilad, Haifa (IL); Semion Khait, Tiberias (IL); Gavriel J. Iddan, Haifa (IL)

(73) Assignee: Given Imaging, Ltd., Yoqneam Ilite (IL)

( * ) Notice: Subject to any disclaimer, the term of this patent is extended or adjusted under 35 U.S.C. 154(b) by 78 days.

(21) Appl. No.: 10/724,109

(22) Filed: Dec. 1, 2003

(65) Prior Publication Data

US 2004/0171915 A1    Sep. 2, 2004

Related U.S. Application Data

(60) Provisional application No. 60/429,562, filed on Nov. 29, 2002.

(51) Int. Cl.
*A61B 1/06*    (2006.01)

(52) U.S. Cl. ..................................... 600/160
(58) Field of Classification Search ................ 600/109, 600/117–118, 160, 473, 476
See application file for complete search history.

(56) References Cited

U.S. PATENT DOCUMENTS

| | | | |
|---|---|---|---|
| 4,278,077 A | 7/1981 | Mizumoto | |
| 5,088,492 A * | 2/1992 | Takayama et al. | 600/431 |
| 5,224,467 A * | 7/1993 | Oku | 600/145 |
| 5,604,531 A | 2/1997 | Iddan et al. | |
| 5,833,603 A | 11/1998 | Kovacs et al. | |
| 5,853,005 A | 12/1998 | Scanlon | |
| 6,074,349 A | 6/2000 | Crowley | |
| 6,165,128 A | 12/2000 | Cespedes et al. | |
| 6,185,443 B1 * | 2/2001 | Crowley | 600/407 |
| 6,240,312 B1 | 5/2001 | Alfano et al. | |
| 6,584,348 B1 | 6/2003 | Glukhovsky | |
| 6,607,301 B1 | 8/2003 | Glukhovsky et al. | |
| 2002/0042562 A1 * | 4/2002 | Meron et al. | 600/361 |
| 2003/0195415 A1 | 10/2003 | Iddan | |

FOREIGN PATENT DOCUMENTS

| | | |
|---|---|---|
| WO | WO 01/50941 | 7/2001 |
| WO | WO 01/65995 | 9/2001 |
| WO | WO 02/054932 | 7/2002 |
| WO | WO03/005877 | 1/2003 |

OTHER PUBLICATIONS

"BBC News Online—Pill camera to 'broadcast from the gut'", Feb. 21, 2000, www.news.bbc.co.uk.

* cited by examiner

*Primary Examiner*—John Leubecker
*Assistant Examiner*—Phillip R Smith
(74) *Attorney, Agent, or Firm*—Pearl Cohen Zedek Latzer, LLP

(57) ABSTRACT

A device, system and method may enable the obtaining of in vivo information other than or in addition to images from for example within body lumens or cavities, such as temperature, pressure, or pH from the gastrointestinal (GI) tract, where the data is typically transmitted or otherwise sent via an optical means to a receiving system.

14 Claims, 9 Drawing Sheets

US 7,118,529 B2

METHOD AND APPARATUS FOR TRANSMITTING NON-IMAGE INFORMATION VIA AN IMAGE SENSOR IN AN IN VIVO IMAGING SYSTEM

CROSS-REFERENCE TO RELATED APPLICATIONS

This application claims the benefit of provisional application No. 60/429,562 filed Nov. 29, 2002 entitled "METHOD AND APPARATUS FOR TRANSMITTING NON-IMAGE DATA IN AN IN VIVO IMAGING SYSTEM" incorporated by reference herein in its entirety.

FIELD OF THE INVENTION

The present invention relates to an in vivo device, system and method for obtaining information from a body lumen; more specifically, to a method and apparatus in an in vivo imaging system for transmitting or sending non-image information.

BACKGROUND OF THE INVENTION

Devices and methods for performing in vivo imaging of passages or cavities within a body, and for gathering information other than image information, are known in the art. These in vivo imaging devices may include, for example, swallowable capsules which collect information and which may transmit the information to a receiver system, endoscopes, etc. These capsules may be utilized to measure for example endo-luminal pH, temperature or pressure throughout the intestines. Such devices may also include, inter alia, various endoscopic imaging systems and devices for performing imaging in various internal body cavities.

An in vivo imaging device may include, for example, an imaging system for obtaining images and other information from inside a body cavity or lumen, such as the GI tract. The imaging system may include, for example, an illumination unit, such as a set of light emitting diodes (LEDs), or other suitable light sources. The device may include an imaging sensor and an optical system, which focuses the images onto the imaging sensor. A transmitter and antenna may be included for transmitting the image signals. A receiver/recorder, for example worn by the patient, may record and store images and other information. The recorded information may then be downloaded from the receiver/recorder to a computer or workstation monitor for display and analysis.

Transmitting both image and non-image information from a sensor (e.g., temperature sensor, pressure sensor, pH sensor, location sensor of the transmitting device, blood detection sensor, or control detector, etc.) may require a broader transmission bandwidth or more complex circuitry, calculation, processing or methods than merely transmitting either one or the other type of such information. Endoscopic devices used for the examination of the body lumens usually transmit (through wired or wireless link) only video (image) information. Addition of sensors to the existing device may require addition to the information transmitted from the endoscopic device. The additional information may require extensive changes in the communication protocol as well as in the communication circuitry of both the transmitting and the receiving ends.

Therefore, there is a need for an in vivo diagnostic device, such as an imaging device and system, which is capable of transmitting non-image information possibly in addition to image information without requiring, for example, changes in the communication protocol.

SUMMARY OF THE INVENTION

An embodiment of the device, system and method of the present invention enables the obtaining of in vivo images and/or non-image data or information from for example from within body lumens or cavities, such as the gastrointestinal (GI) tract. An embodiment of the device, system and method of the present invention enables the transmission of non-image information from within body lumens or cavities, such as the gastrointestinal (GI) tract, via an image sensor or other light detecting sensor. According to an embodiment of the invention, output from a non-image sensor may be converted to an optical output that may be relayed to an image sensor or other light detecting sensor.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn to scale. For example, the dimensions of some of the elements may be exaggerated relative to other elements for clarity, or several physical components may be

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Using a device, system and method according to some embodiments of the present invention, non-image information may be transmitted possibly along with image information (or with other information such as light intensity information). This may be done in some embodiments without requiring, for example, reconfiguration of the in vivo processor and/or transmitter and an external receiver to interleave transmission of both image and non-image information. The structures that may already exist in an imaging device or endoscope, for example, may be used to collect and transmit non-image information. According to one embodiment of the invention non-image information may be efficiently sent using typically unused pixels in the image sensor. Other suitable methods for transmitting non-image information through the image sensor may be implemented.

Embodiments of the device, system and method of the present invention are typically used in conjunction with an in vivo imaging system or device such as embodiments described in U.S. Pat. No. 5,604,531 to Iddan et al. and/or in publication number WO 01/65995 entitled "A Device And System For In Vivo Imaging", published on 13 Sep. 2001, both of which are hereby incorporated by reference. However, the device, system and method according to the present invention may be used with any device, system and method providing imaging and other information from a body lumen or cavity.

Figure 1:
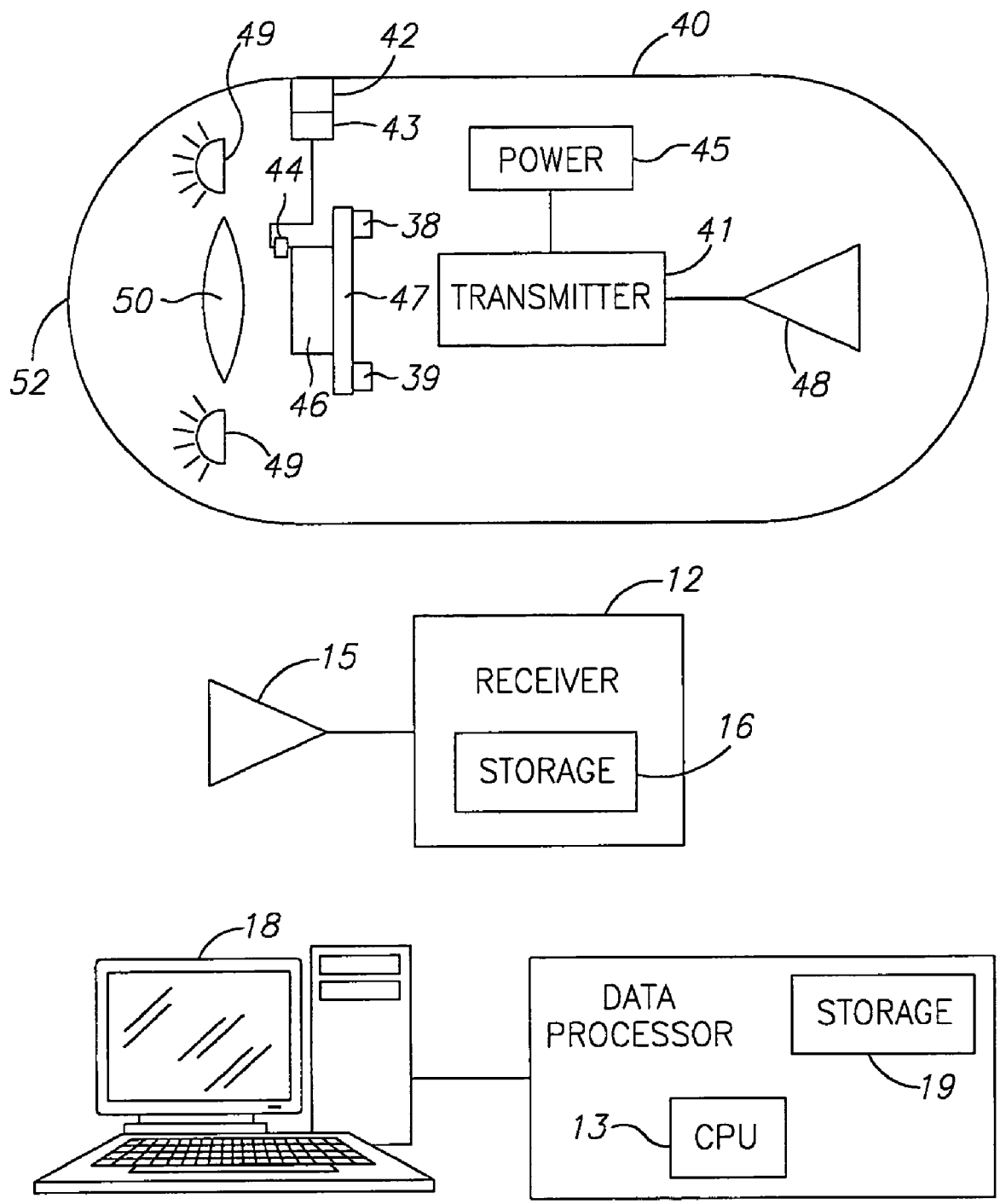
FIG. 1 shows a schematic diagram of an in vivo imaging system according to one embodiment of the present invention.

Reference is made to FIG. 1, which shows a schematic diagram of an in vivo imaging system according to one embodiment of the present invention. In an exemplary embodiment, an in vivo device 40 may be for example a swallowable capsule capturing images and other information from within a body lumen, typically the GI tract. In other embodiments of the invention, device 40 need not be swallowed, need not be capsule shaped, and may be maneuvered through or positioned in body lumens or cavities other than the GI tract. Further, devices, systems and methods according to embodiments of the present invention need not be used in conjunction with humans or animals; for example devices, systems and methods according to embodiments of the present invention may be used in conjunction with imaging or collecting data from machines, pipes, etc. Typically, device 40 includes, for example, at least one sensor such as an image sensor 46, for capturing images, power source 45, an optical system 50, illumination source 49 such as an LED, at least one other (non-image) sensor 42 (such as a temperature sensor, a pH sensor, a pressure sensor, or a control detector to obtain information pertaining to the state or functioning of the device 40 such as battery level detector, signal strength detector, operational mode detector, etc.) for capturing non-image information, an optional illumination device driver circuit 43, an sensor illumination source 44, and an optional processing chip or circuit 47 for processing the signals generated by the image sensor 46. An optical dome 52 provides a generally transparent cover for the optical elements, provides a sealed barrier to bodily fluids, and may perform other functions (such as holding optical elements). Optical system 50 may include, for example, one or more optical elements (not shown), such as one or more lenses or composite lens assemblies (not shown), one or more suitable optical filters (not shown), or any other suitable optical elements (not shown), may aid in focusing reflected light onto the image sensor 46 and performing other light processing. Typically, the optical system 50 may produce a circular image, but other image shapes may be produced. Device 40 may be, for example, similar to embodiments described in U.S. Pat. No. 5,604,531 and/or WO 01/65995, described above. Embodiments of the device 40 are typically autonomous and are typically self-contained. For example, the device 40 may be a capsule or another unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source. However, the device may be any sort of in vivo sensor device and may have other configurations. For example, the device may be an endoscope. Light detecting sensors other than image sensors may be used.

Processing circuit 47 need not be a separate component; for example, processing or a processing chip may be integral to the image sensor 46 or transmitter 41. In one embodiment of the invention, illumination source 49 and sensor illumination source 44 may be single illumination source, employed for illumination of a target object (not shown) to be imaged as well as for conveying an output from non-image sensor.

Device 40 typically includes a transmitter 41, for transmitting image information to a receiving device, and may include other components, such as, for example, a memory module 39 or a compression module 38, for compressing information. The transmitter 41 may transmit image information as well as other information (i.e., non-image information). The transmitter 41 may be typically an ultra low power radio frequency (RF) transmitter with high bandwidth input, possibly provided in chip scale packaging. Other suitable transmitters may be used. The transmitter may transmit via an antenna 48. The transmitter 41 may also include circuitry and functionality for controlling the device 40. Typically, the device includes a power source 45, such as one or more batteries. For example, the power source 45 may include silver oxide batteries, lithium batteries, or other electrochemical cells having a high energy density, or the like. Other power sources may be used.

Other components and sets of components may be used. For example, the power source may capable of receiving power from an be an external power source transmitting power to the device 40, and a controller separate from the transmitter 41 may be used. In one embodiment, the image sensor 46 may be a complementary metal oxide semiconductor (CMOS) image sensor. The CMOS image sensor may be typically an ultra low power image sensor and may be provided in chip scale packaging (CSP). Other types of CMOS image sensors may be used. In another embodiment, another image sensor may be used, such as a CCD image sensor, or other image sensors. Typically, the image sensor 46 may be rectangular in shape (e.g., a 256×256 square CMOS array). Other suitable shapes and array sizes may be used. An imaging device need not be used; for example output from a non-image sensor may be converted to an optical output and input to, for example, a simple light detector, the output of which may be relayed to an external receiver.

Preferably, located outside the patient's body in one or more locations, may be a receiver 12, preferably including an antenna or antenna array 15, for receiving image and possibly other information from device 40, a receiver storage unit 16, for storing image and other information, a data processor 14, a data processor storage unit 19, and an image monitor 18, for displaying, inter alia, the images and other information transmitted by the device 40 and recorded by the receiver 12. Typically, the receiver 12 and receiver storage unit 16 may be small and portable, and may be worn on the patient's body during recording of the images. Typically, data processor 14, data processor storage unit 19 and monitor 18 are part of a personal computer or workstation, which may include standard components such as a processor 13, a memory (e.g., storage 19, or other memory), a disk drive (not shown), and input-output devices (not shown), although alternate configurations are possible. In alternate embodiments, the data reception and storage components may be of another configuration; for example the receiver 12 and/or receiver storage unit 16 may be an integral part of a personal computer or workstation. It should be emphasized that other embodiments may include a wired rather than wireless device, such as a wired endoscope. In this case, certain elements shown in FIG. 1 may be omitted, such as for example transmitter 41, antenna 48, antenna array 15 and receiver 12.

The receiving and recording components may be, for example, similar to embodiments described in U.S. Pat. No. 5,604,531 and/or WO 01/65995, described herein. However, the receiving and recording components may be of other configurations.

Typically, the device 40 transmits information (e.g., image information) in discrete portions. Each portion typically corresponds to an image or frame. For example, the device 40 may capture an image once every half second, and, after capturing such an image, transmit the information to the receiving antenna. Other suitable capture rates and transmission methods may be employed. Typically, the image information recorded and transmitted may be digital color image information, although in alternate embodiments other image formats (e.g., black and white image information) may be used. In one embodiment, each frame of image information includes 256 rows of 256 pixels each, each pixel including information for color and brightness, according to known methods. For example, in each pixel, color may be represented by a mosaic of four sub-pixels, each sub-pixel corresponding to primaries such as red, green, or blue (where one primary may be represented twice). The brightness of the overall pixel may be recorded by, for example, a one byte (i.e., 0–255) brightness value. Other data formats may be used, and other image formats may be used.

Typically, the image sensor 46 may be rectangular (more typically and more specifically square) in shape, and the image produced by the optical system 50 may be typically substantially circular in shape. Other image shapes may be produced, such as for example irregular shapes, diamond, ovals, etc. Where the image produced by the optical system 50 does not entirely fill the typically rectangular image sensor 46, there may be areas of the image sensor 46 (e.g., corner 53 in FIG. 2) that may not be used to receive image information. According to an embodiment of the present invention, non-image information obtained from a non-image sensor 42 may be sampled using one or more of these specified or other areas otherwise not designated to capture image information. According other embodiments of the invention, non-image information may overlap or be integrated onto an area used to capture image information. Alternately, areas of the image sensor typically used to receive image information may be reduced or otherwise altered to accommodate for the conveying of one or more streams of non-image information.

Figure 2:
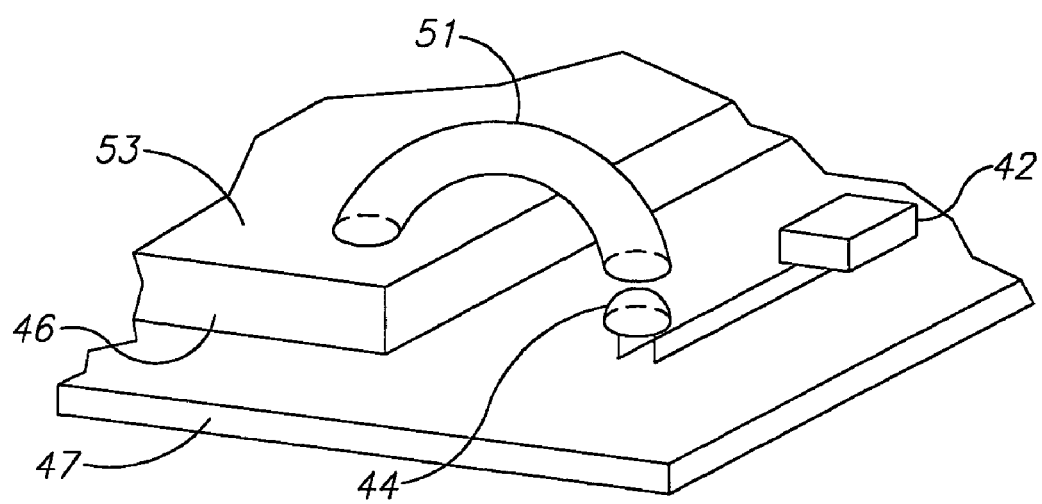
FIG. 2 depicts a schematic enlargement of one embodiment of the present invention.

FIG. 2 depicts an embodiment of the invention. The in vivo device (e.g., device 40, or another suitable device) measures or observes the non-image information using for example, a sensor 42 (e.g., a thermometer). The sensor 42 typically may express its output as an electrical quantity, such as voltage. For example, a temperature sensor may produce 50 mV DC per temperature change of 1° C. A miniature pressure sensor (e.g. by Endveco, model 8507C) may be used and may measure pressure in range of 2 to 50 pounds per square inch, with the full range output of 300 mv. The output from the non-image sensor 42 can be in other suitable forms, such as a signal, frequency, bit pattern, pulse repetition, pulse width, etc. Non-image sensor 42 may be a known temperature sensor such as the temperature sensor used by the Coretemp™ device. Of course, other suitable sensors may be used as well.

This electrical signal or quantity produced by the sensor 42 may be relayed to one or more sensor illumination sources 44 (such as, for example, "white" or monochromatic LEDs, although other suitable types of illumination sources may be used) such that the variation in voltage or other signal aspect produces a variation in optical output (e.g., color, brightness, etc.) of the LED or, for example when using more than one LED or light source the output may be expressed by the combination of LEDs in an on or off state. Sensor 42 may be electrically connected, or connected to transmit information in another manner, with sensor illumination source 44, possibly via intermediate circuits such as processing units, driver circuits, etc. The electrical signal or quantity may be converted to another modality which may be expressed with light; for example, light intensity, light frequency, light pulse amplitude, light pulse width, light pulse frequency or other suitable modalities. The electrical signal or quantity may be relayed to the sensor illumination source 44 directly, or for example, (as shown in FIG. 2) indirectly through for example an illumination device driver circuit 43. The illumination device driver circuit 43 may be external or incorporated into the processor 47 or sensor 42. The output of the sensor may modulate or convert the sensor illumination source in different manners, including for example, light intensity modulation, light frequency (color) modulation, light pulses repetition modulation, light pulses width modulation, etc. In one embodiment of the invention, two or more unused corners or other specified areas of the image sensor 46 may be illuminated in different combinations or different color combinations, based on threshold quantities of the sensors output.

Figure 3:
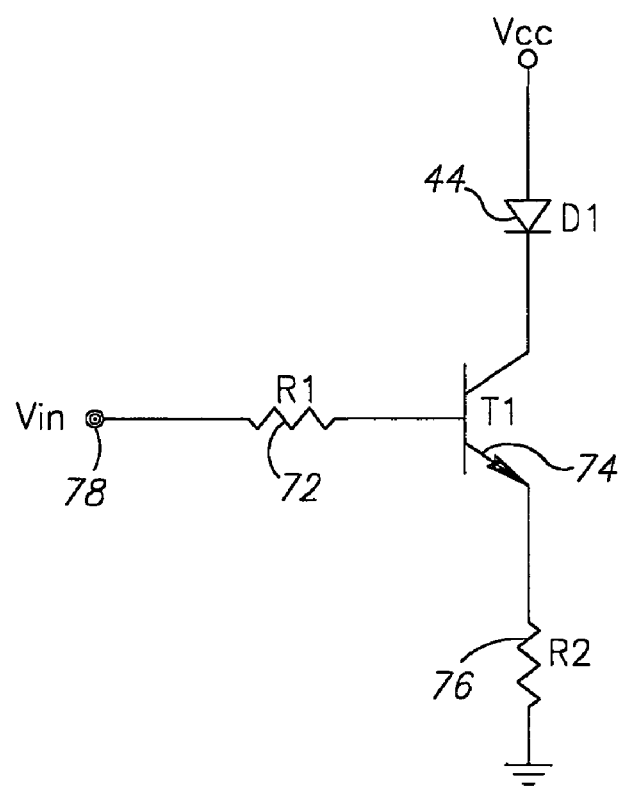
FIG. 3 depicts an illumination device driver circuit that may be used in connection with an embodiment of the present invention.

FIG. 3 is an example of an illumination device driver circuit with sensor illumination source 44 that may be used in connection with an embodiment of the present invention. Other suitable circuits or processing systems may be used. LED 44 provides illumination proportional to the driving voltage at terminal 78. The driver is based on the transistor amplifier 74 with two resistors 72 and 76, whose characteristics determine the working point. The illumination from the sensor illumination source 44 may be relayed via, for example, an optical guide 51 (e.g., an optical fiber, plastic conduit, prism, mirror, etc.) to a typically unused area of the image sensor 46 (e.g., a corner, although other areas may be used). The sensor illumination source 44 and/or any optical equipment (e.g., optical guide 51) associated with the sensing illumination source may be covered or associated with shielding (e.g., a baffle, a coating) (not shown) to prevent interference with the image information being sensed at the image sensor or with light provided by other illumination sources. Other methods of conveying light from the sensor illumination source 44 may be used. For example, no light guide need be used, and/or the sensor illumination source 44 may be mounted directly on the image sensor 46.

Thus, for example, a low voltage output from the sensor 42 (e.g., caused by a low temperature sensed) may modulate the sensor illumination source 44 to light dimly, while a high voltage output from the sensor 42 (e.g., caused by a high temperature sensed) may cause the sensor illumination source 44 to light brightly. Of course, the correspondence between sensed modality (e.g., temperatures) and output light signal may be reversed. This illumination (which varies with the non-image information read by sensor 42) is received at the image sensor 46, possibly processed, and transmitted and received together with the image information. In another example, a low voltage output from sensor 42 may modulate the sensor illumination source to emit light in one color, while a high voltage output from sensor 42 may modulate the sensor illumination source to light in a second color. In yet another example when employing more than one sensor illumination source, a high voltage output from a sensor 42 reaching above a defined threshold may be represented by illuminating for example two sensor illumination sources substantially simultaneously, while a low reading may be represented for example by illuminating only one illumination source. Other suitable combinations may be used using more than one threshold and more than two sensor illumination sources. A combination of different intensities, frequencies, and number of sensor illumination sources may be used to convey the output of one or more sensors such as sensor 42. The output of more than one non-image sensor may be conveyed simultaneously by using more than one sensor illumination source or by modulating two or more properties of a sensor illumination source. For example, one non-image sensor output may be conveyed by light frequency while a second non-image sensor output may be conveyed by light intensity. The optical non-image information may be, for example, processed, or interpreted at the receiver 12 and/or at the data processor 14. The non-image information may be displayed as raw or interpreted image information.

Figure 4:
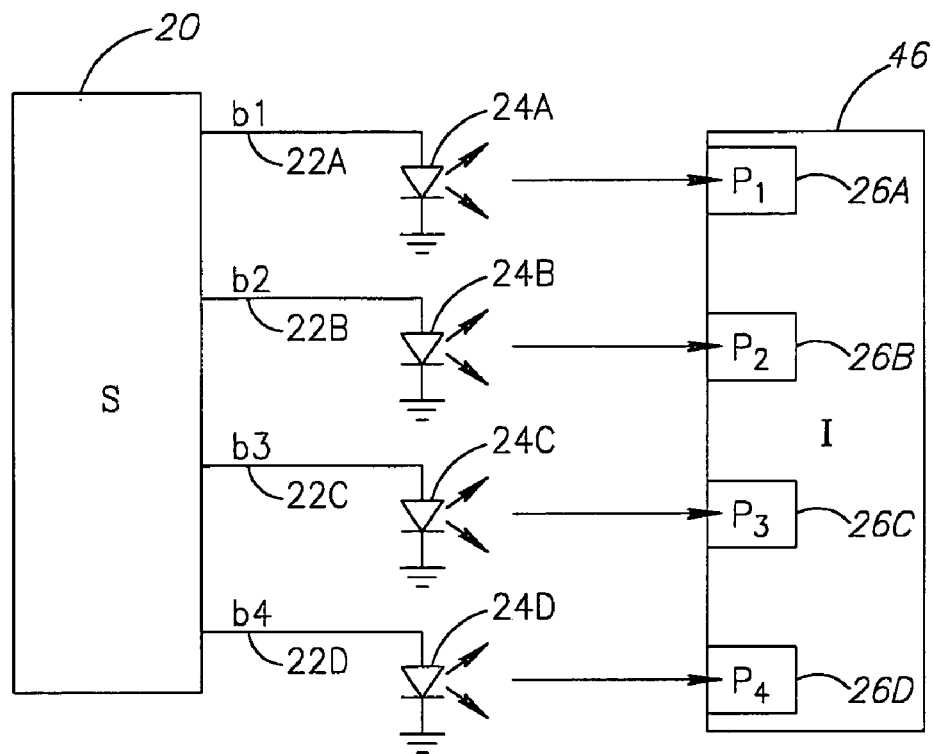
FIG. 4 depicts a circuit for translation of a digital output of a non-image sensor according to one embodiment of the present invention.

FIG. 4 is an example of a digital output 22A–D from a non-image sensor 20 that may be conveyed through four LEDs 24A–D, according to one embodiment. Other suitable digital outputs and number of LEDS may be used as well. If sensor 20 has a binary bus 22A–D, each bit of it may be connected to individual LEDs 24A–D, illuminating separate pixels or separate areas 26A–D on the image sensor 46. The digital output of sensor 20 may be reconstructed based on for example the following equation (other suitable coding schemes and equations may be used):

$$\text{Digital Sensor Output} = P1 + 2*P2 + 4*P3 + 8*P4.$$

Where one or more of the outputs: P1, P2, P3, or P4 may equal one if the illumination of their respective LED is greater than a given threshold and zero if the illumination of their respective LED is less than that given threshold. Alternatively one or more of the outputs: P1, P2, P3, P4 may equal zero if the illumination of the respective LED is greater than a given threshold and equal to one if the illumination of the respective LED is less than that given threshold. Other number may be used. An analog sensor may be incorporated in this embodiment by adding for example an A/D converter to convert an analog output to a digital output. In one exemplary embodiment, two or more bits may be represented with one sensor illumination source such as one LED. For example, a specified level of intensity may convey the output of one bit while a specified light frequency may convey the output of a second bit. Other suitable parameters and methods may be employed as well.

Figure 5:
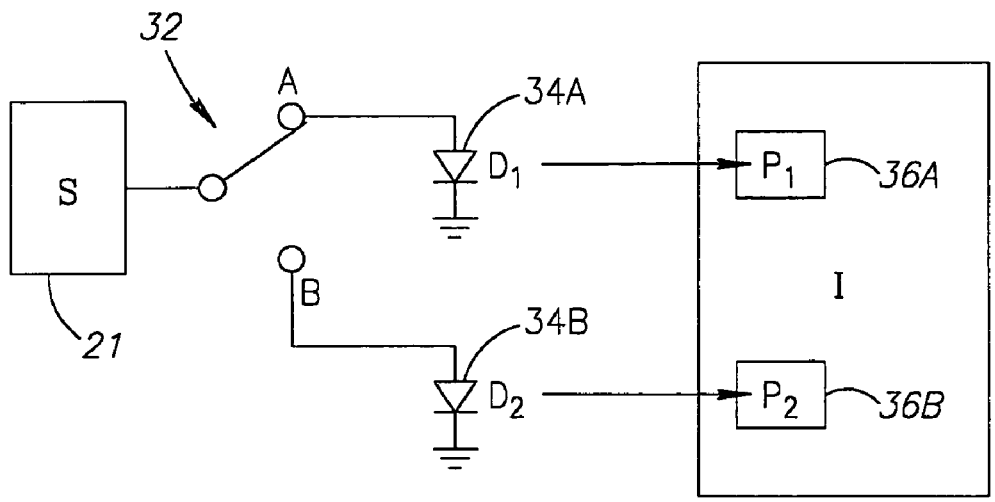
FIG. 5 depicts a circuit for sampling a non-image sensor at a different rate than image capture frame rate according to one embodiment of the present invention.

FIG. 5 is an example of an embodiment where a non-image sensor 21 may be sampled at a different rate than the frame capture rate of the image sensor 46. Switch 32, for example a toggle switch, connected on one end to the output of non-image sensor 21 and on the other end to one out of the at least two sensor illumination sources 34A and 34B. Switch 32 may be in position A at time t1 so that sensor 21 may be, for example, sampled by LED 34A, illuminating pixel or area 36A in image sensor 46. At time t2, toggle switch 32 may be in position B so that sensor 21 may be for example sampled by LED 34B, illuminating pixel or area 36B in image sensor 46. With two LED 34A and 34B, the non-image sensor 21 may be sampled at twice the frequency of the image capture rate. Other suitable sampling rates and number of LEDs may be used as well. In an alternate embodiment, the non-image sensor may be sampled at a lower rate the image. Non-image sensor may be sampled for example every other frame or at any other suitable rate.

Figure 6:
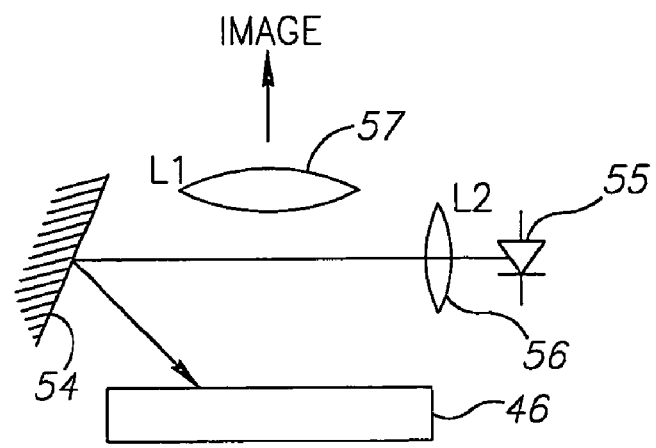
FIG. 6 shows a schematic diagram of an image sensor used interlacingly to sample both imaging and non-imaging information according to one embodiment of the present invention.

FIG. 6 is an example of an embodiment using interlacing to sense both image information and non-image information in the same image sensor area. In this exemplary embodiment, the imager sensor may for example sample image information and non-image information in alternate frames. For example, even images may be used for imaging and odd images may be for example used for non-image sensing. Other suitable combinations may be used for example every third image may be used for sensing or alternatively for imaging. Other frequencies of image and non-image capturing may be employed. In this exemplary embodiment, illumination of sensing LED(s) 55 are driven by a non-image sensor and are focused on to image sensor 46 using an optical system 56 and for example mirror 54. Mirror 54 may be used to direct illumination of sensing LED 55 toward image sensor 46, for example, when sensing LED may be positioned away from the line of sight of image sensor 46. During non-image sampling the illuminating LED(s) (not shown) used for imaging are turned off, so that only the illumination of the sensing LED(s) 55 may be captured by the image sensor. During imaging, the sensing LED(S) 55 are turned off so that images may be focused onto image sensor 46 via for example second optical system 57. Different configurations may be used that do not require an optical system 56 or mirror 54 for focusing sensing illumination onto image sensor 46.

Figure 7:
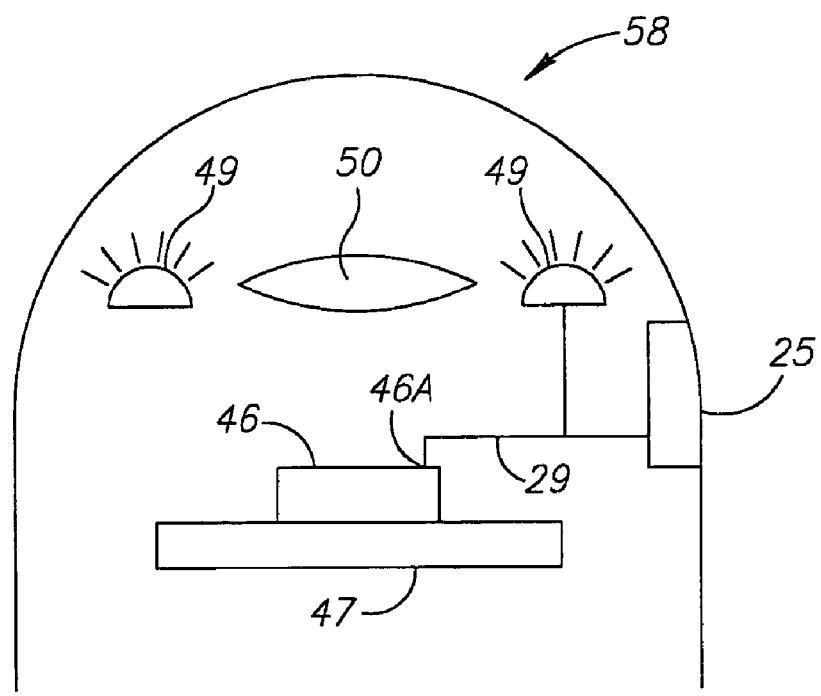
FIG. 7 shows a schematic diagram of an optical head of an in vivo imaging system according to another embodiment of the present invention.

FIG. 7 is a schematic diagram of an optical head 58 of an in vivo imaging system according to another embodiment of the present invention. In this exemplary embodiment, a non-image sensor has an optical output for example a temperature sensitive liquid crystal sensor 25 where the color of sensor 25 may be a function of temperature and may change color in response to a change in temperature. One or more light guide(s) 29 (e.g., an optical fiber, plastic conduit, prism, mirror, etc.) may direct light from illumination source (s) 49 to sensor 25 and direct reflected light from sensor 25 to a specified location 46A on image sensor 46. The color of sensor 25 may be recorded in such a manner in a specified location on an image obtained from image sensor 46. In another exemplary embodiment, an illumination source other than illumination source 49 may be used to illuminate sensor 25.

Figure 8:
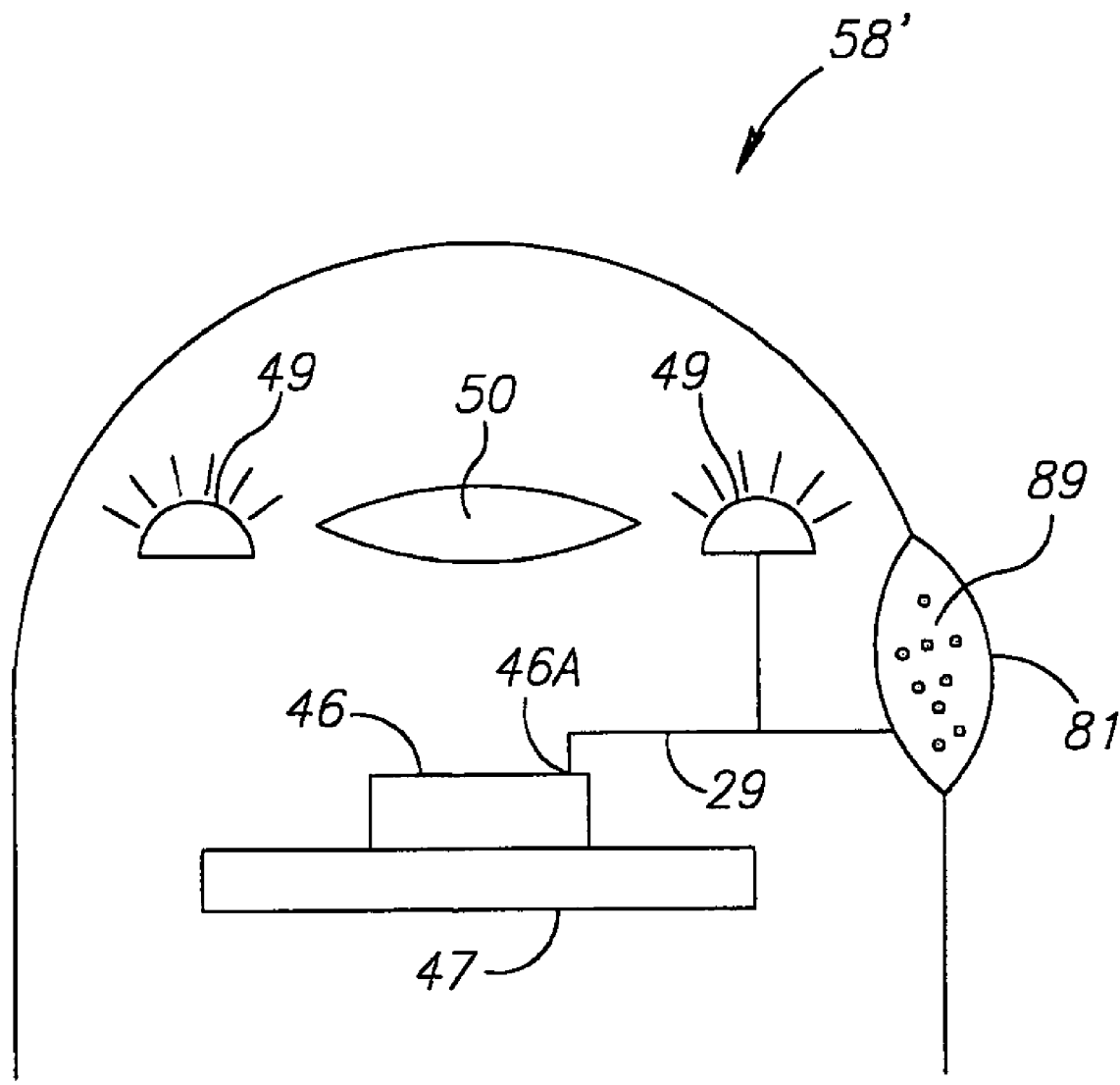
FIG. 8 shows a schematic diagram of an optical head of an in vivo imaging system according to yet another embodiment of the present invention.

FIG. 8 shows a schematic diagram of the optical head 58' of an in vivo imaging system according to another embodiment of the present invention. In this exemplary embodiment, a non-image sensor has an optical output for example a pH sensitive agent encapsulated in a semi-permeable membrane 81. As bodily fluids diffuse in and out of at least partially transparent semi-permeable membrane 81, a pH sensitive agent 89 changes color in accordance to the pH level of the fluid diffusing through membrane 81. One or more light guide(s) 29 may direct light from illumination source 49 to membrane 81 and direct reflected light from membrane 81 to a specified location 46A on image sensor 46. The color of pH sensitive agent 89 may be recorded in such a manner in a specified location on an image obtained from image sensor 46. Other sensors with optical outputs may be used as well. For example a sensor where the output is conveyed by a change in polarization, a change in color, a change in shape or a change in orientation may be used.

In one embodiment of the invention, the current mode of operation of the transmitting device may be conveyed, for example the specific image sensor currently transmitting images may be conveyed in the case where a plurality of image sensors are incorporated in a single transmitting device (see for example a multiple image sensor device such as in some embodiments described in WO 02/054932 entitled SYSTEM AND METHOD FOR WIDE FIELD IMAGING OF BODY LUMENS, which is hereby incorporated by reference) or for example in a case where a plurality of transmitting devices are being employed concurrently. In one embodiment of the invention for example, features of the device (e.g., motility detection or localization in the GI tract, blood detection in the lumen content etc.) may be conveyed. Mode of operation and features of the transmitting device may be conveyed in a similar manner as has been described herein for conveying non-image sensor information. For example, light intensity, light frequency, light pulse amplitude, light pulse width, light pulse frequency or other suitable modalities may be used to convey mode of operation and features of the transmitting device. For example in the case where two imaging devices are being employed concurrently, one transmitting device may be identified with one or more lit LED(s) or other light producing unit(s) displayed in the corner or other area of transmitted image while the other transmitting device may be identified with a non-lit LED or an LED lit at a lower intensity or lit with a different color. More than one LED may be used at a time, lit in different combinations to convey a specific mode or operation or feature of the transmitting device.

Figure 9A:
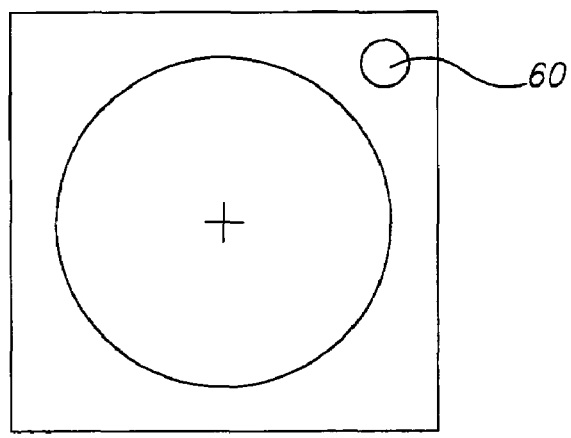
FIGS. 9A, 9B and 9C depict examples used for displaying the information obtained in connection with an embodiment of the present invention.
Figure 9B:
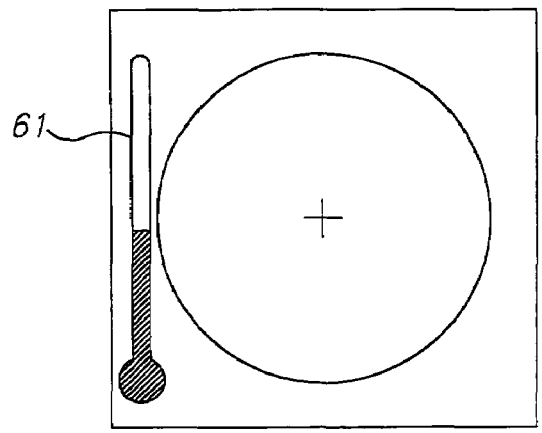
Figure 9C:
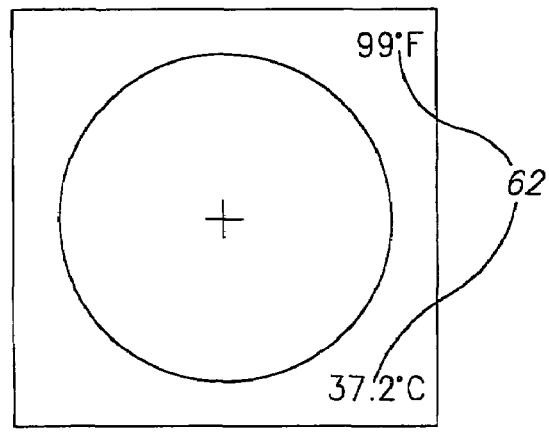

FIGS. 9A, 9B and 9C are some possible displays of the non-image information according to various embodiments: for example, as a lit or otherwise indicated area 60 on the monitor or display outside the image, a graphical icon 61 or a numerical value 62. In FIG. 9A, the portion of the image sensor that is lit by the sensor illumination source is displayed as an illuminated area on a corresponding area of the monitor. A quality of the illuminated area 60 (e.g., brightness, color) may thus vary with the non-image information sensed by non-image sensor 42. Alternately, data processor 14 can, for example, take the brightness or color information on a certain area of the image corresponding to the spot and process it. For example, the illumination information may be transformed into a numerical value and displayed as a numerical value 62 (as shown in the embodiment of FIG. 9C) or a graphical icon 61 (as shown the embodiment of FIG. 9B). The illuminated area 60, numerical value 62 or graphical icon 61 may typically vary or change along with the time elapsed or corresponding image frame. Other methods of displaying the non-image information may be used. In other embodiments, other suitable sensing devices may be used sensing or providing information on other parameters, such as pressure, pH, location, power level, etc.

Figure 9D:
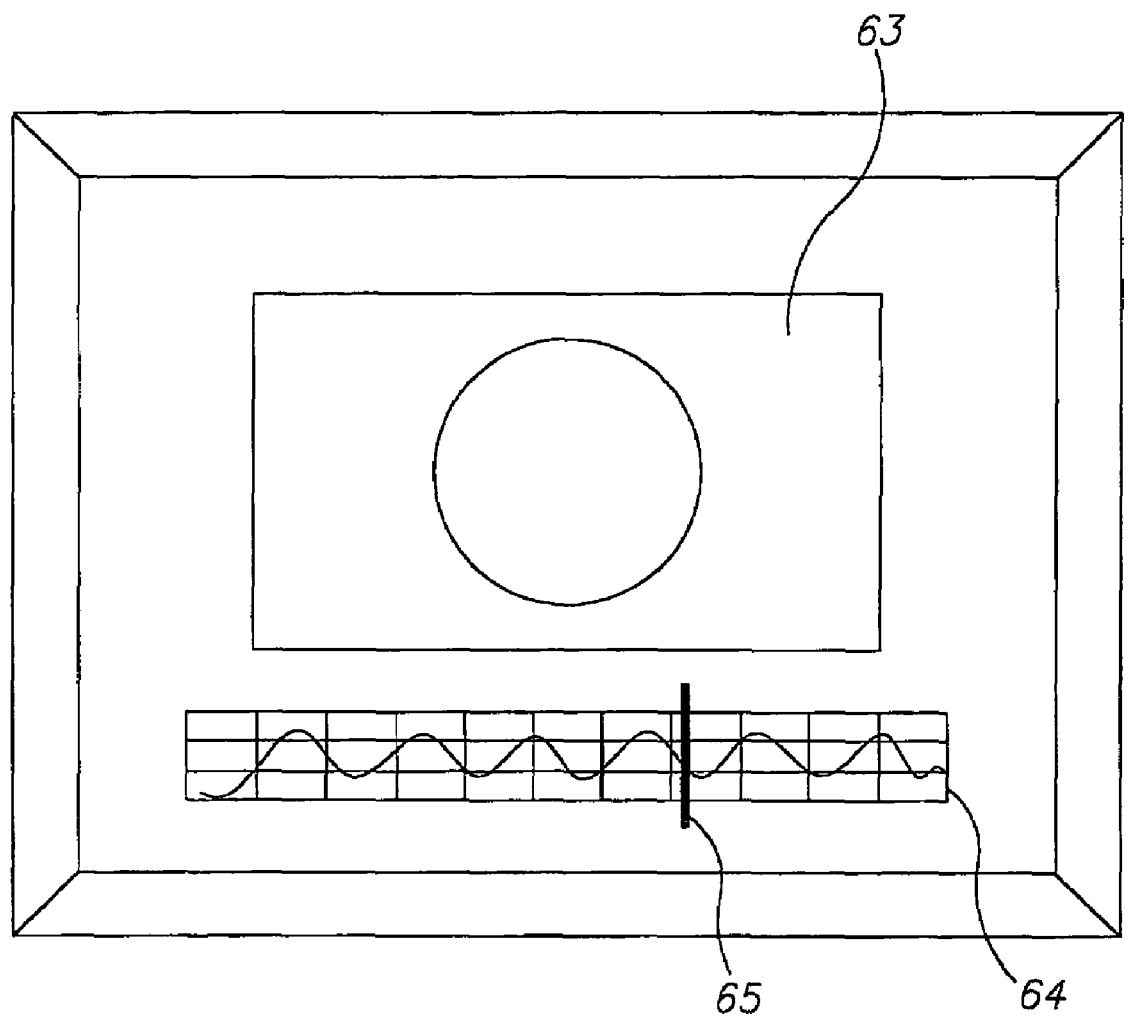
FIG. 9D shows a sample graphical user interface (GUI) of video endoscope with additional non-video data according to one embodiment of the invention.

The non-image information may also be displayed as graphical information in other parts of the display or monitor besides the image area. The area on the image sensor used for the non-image information may be masked by for example black mask in the Graphic User Interface and the non-image information may be processed and displayed in another portion of the display. For example, FIG. 9D shows image information 63 and a graph of non-image information 64 over time. While the image information is being run by the user, the marker 65 may show the corresponding value of the non-image information.

Figure 10A:
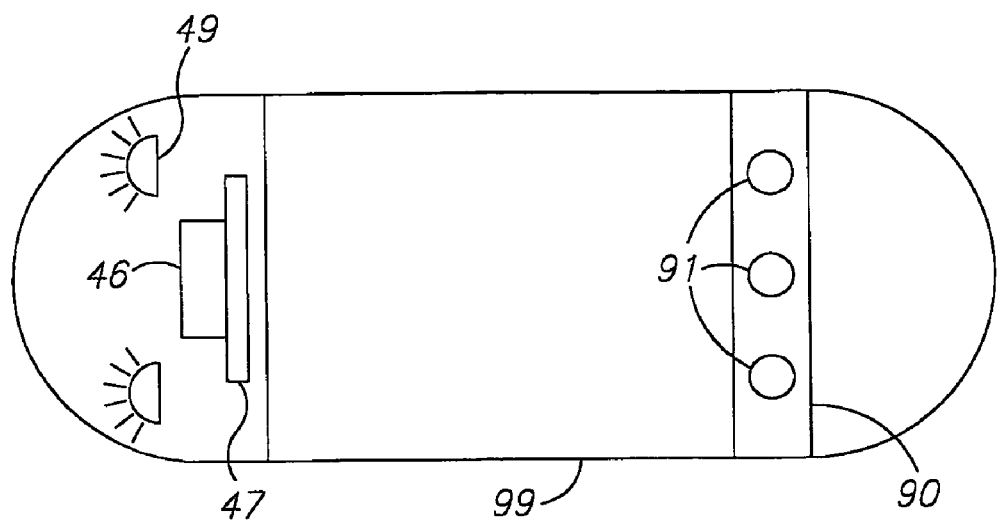
FIG. 10A shows a schematic diagram of an in vivo imaging system with two image sensors according to another embodiment of the present invention.
Figure 10B:
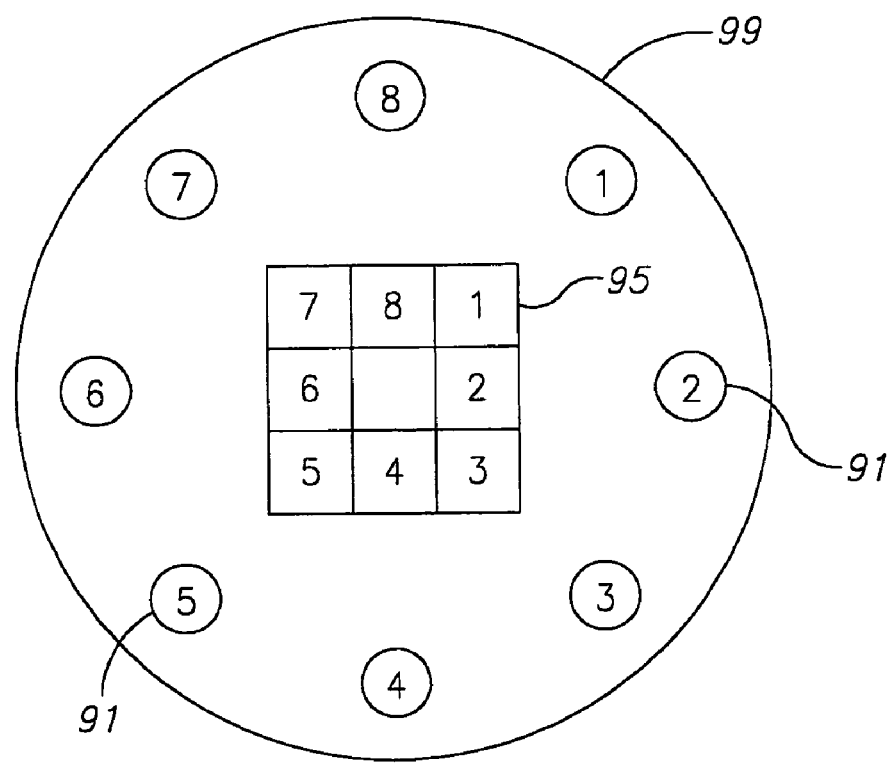
FIG. 10B shows a schematic diagram of a cross-sectional view of an in vivo imaging system with multiple image sensors according to an embodiment of the present invention.

FIG. 10A is a schematic diagram of the outer surface of an in vivo imaging device according to one embodiment of the present invention. In this embodiment a ring 90 with non-image sensors 91 surround the device 99 which may be, for example, capsule shaped, but which may have other suitable structures. In an alternate embodiment of the invention, the sensors may be positioned on the device in an arrangement other than a ring. Light detecting sensor 95 (FIG. 10B) may be entirely devoted to capturing non-image information. In one embodiment of the invention, light detecting sensor may be an image sensor. FIG. 10B is a schematic diagram showing a top view of light detecting sensor 95 and a set of surrounding non-image sensors 91. Each of sensors 91 may be optically guided (e.g. using an optical fiber, plastic conduit, prism, mirror, etc.) to a specific location on light detecting sensor 95. The output of sensors 91 may all have electrical outputs conveyed to an illuminating device, optical outputs (e.g. liquid crystal temperature sensor, and pH sensor (FIG. 8), other outputs or a combination of outputs. In one embodiment of the invention a second image sensor 46 is positioned on the other end of device 99 and may be devoted entirely to imaging. The transmission rate of light detecting sensor 95 may be the same or a different rate than the image sensor 46. In another embodiment of the invention, light detection sampling of non-image information or other activation of light detecting sensor 95, may be triggered by an event captured in image sensor 46. As such, processor 47 may be electrically connected to light detecting sensor 95 or its transmitting line (not shown) through a triggering switch (not shown). Alternatively, the image sensor 46 may be triggered based on an output or an event or a combination of outputs or events sampled by one or more non-image sensors. As such the output of one or more non-image sensors may be electrically connected to image sensor 46 or its transmitting line (not shown) through a triggering switch.

Figure 11:
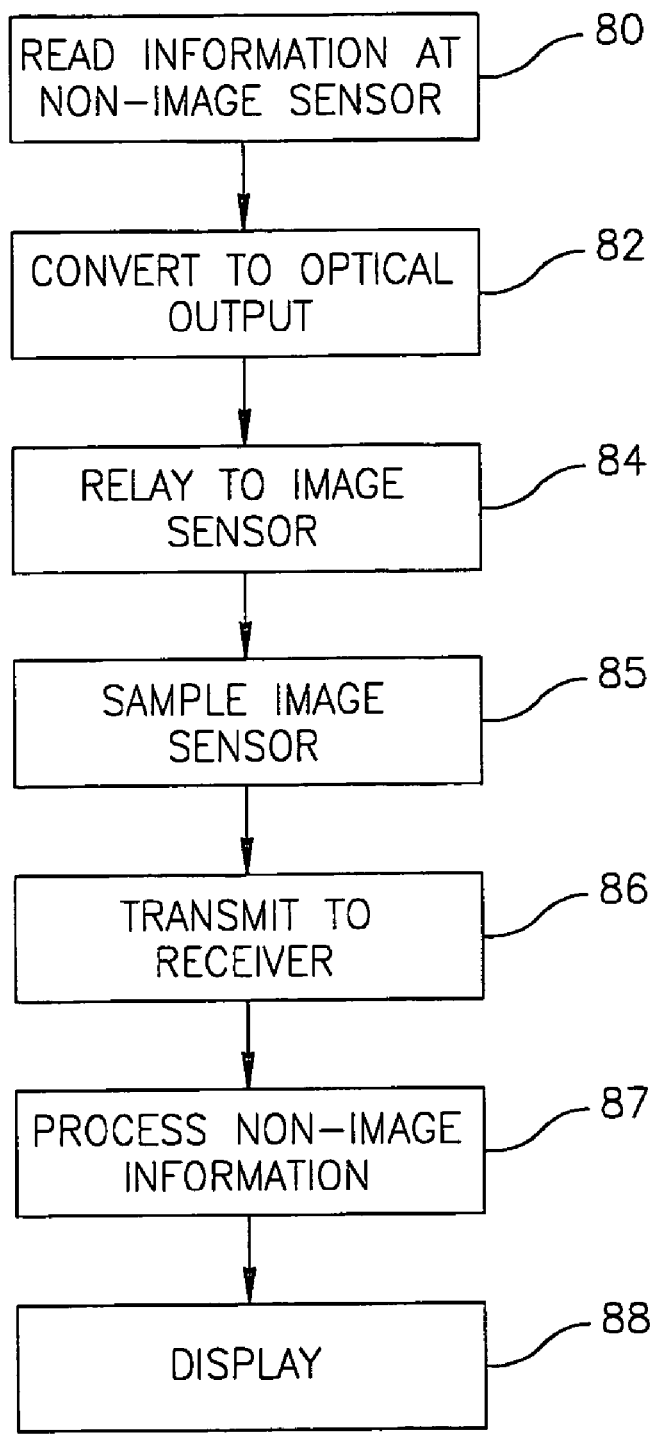
FIG. 11 depicts a series of steps of a method according to an embodiment of the present invention.

FIG. 11 depicts a series of steps of a method according to an embodiment of the present invention. At step 80, non-image information may be obtained or read, sampled or sensed. At step 82 (optional), the electrical signal or other quantity or output corresponding to the non-image information sensed may be converted into an optical output (e.g.

modulated optical output). At step 84, modulated optical output may be relayed or directed to a specific location on image sensor. At step 85, image sensor may be sampled. At step 86, the sampled image information may be transmitted (including the non-image information) to a receiver. At optional step 87, the non-image information incorporated in the image information may be interpreted. Interpretation may include for example converting light intensity, color, or pattern information to a digital or analog output representing the level of a parameter originally sensed by a non-image sensor or a feature or status of the device. The digital or analog output may for example be an absolute value representing the level of a parameter sensed or alternatively may be a relative value representing for example a ratio. At step 88, the non-image information may be processed and possibly displayed. Other suitable steps or series of steps may be used.

While the invention has been described with respect to a limited number of embodiments, it will be appreciated that many variations, modifications and other applications of the invention may be made. Embodiments of the present invention may include apparatuses for performing the operations herein. Such apparatuses may be specially constructed for the desired purposes (e.g., a "computer on a chip" or an ASIC), or may include general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular device, capsule, image sensor, computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language.

It will be appreciated by persons skilled in the art that the present invention is not limited to what has been particularly shown and described hereinabove. Rather the scope of the present invention is defined only by the claims, which follow:

The invention claimed is:

1. A method for transmitting in vivo non-image information, the method comprising:
    obtaining non-image sensor information from a sensor;
    relaying the non-image sensor information to an illumination source contained within a container, wherein the non-image sensor information is used for modulating either the frequency of the optical output of the illumination source or the amplitude for changing the brightness of the optical output of the illumination source;
    relaying the output of the illumination source to an area on an image sensor, the image sensor contained within the container; and
    transmitting the image sensor information to an external receiver.

2. A method for transmitting in vivo non-image information, the method comprising:
    obtaining non-image sensor information from a sensor;
    relaying the non-image sensor information to an illumination source contained within a container, wherein the non-image sensor information is used for modulating the frequency of the optical output of the illumination source for changing the brightness of the optical output of the illumination source;
    relaying the output of the illumination source to an area on an image sensor, the image sensor contained within the container; and
    transmitting the image sensor information to an external receiver.

3. A method for transmitting in vivo non-image information, the method comprising:
    obtaining non-image sensor information from a sensor;
    relaying the non-image sensor information to an illumination source contained within a container, wherein the non-image sensor information is used for modulating the amplitude of the optical output of the illumination source for changing the brightness of the optical output of the illumination source;
    relaying the output of the illumination source to an area on an image sensor, the image sensor contained within the container; and
    transmitting the image sensor information to an external receiver.

4. A method according to one of claims 1, 2, or 3 comprising: displaying image sensor information.

5. The method according to one of claims 1, 2, or 3 wherein the non-image sensor information is obtained from the gastrointestinal tract.

6. The method according to one of claims 1, 2, or 3 comprising: directing the non-image sensor information to a specified location on the image sensor via an optical guide.

7. The method according to one of claims 1, 2, or 3 wherein relaying the non-image sensor information to an illumination source is achieved by electrically connecting the illumination source to the non-image sensor.

8. The method according to one of claims 1, 2, or 3 comprising the step of interpreting the non-image information obtained.

9. The method according to claim 8 comprising the step of displaying the interpreted non-image sensor information.

10. An in vivo imaging system comprising:
    a non-image sensor to obtain non-image information;
    a container enclosing:
    an illumination source;
    an illumination driver circuit for relaying the non-image sensor information to an illumination source, wherein the non-image sensor information is used for modulating either the frequency of the optical output of the illumination source or the amplitude for changing the brightness of the optical output of the illumination source; and
    an imager to image at least the output of the illumination source.

11. An in vivo imaging system comprising:
    a non-image sensor to obtain non-image information;
    a container enclosing;
    an illumination source;
    an illumination driver circuit for relaying the non-image sensor information to an illumination source, wherein the non-image sensor information is used for modulating the frequency of the optical output of the illumination source for changing the brightness of the optical output of the illumination source; and an imager to image at least the output of the illumination source.

12. An in vivo imaging system comprising:
a non-image sensor to obtain non-image information;
a container enclosing;
an illumination source;
an illumination driver circuit for relaying the non-image sensor information to an illumination source, wherein the non-image sensor information is used for modulating the amplitude of the optical output of the illumination source for changing the brightness of the optical output of the illumination source; and an imager to image at least the output of the illumination source.

13. The in vivo system of one of claims 10, 11, or 12 comprising a display to display the relayed non-image sensor information.

14. The in vivo system according to one of claims 10, 11, or 12 comprising a processor to process the relayed non-image sensor information imaged by the imager.

* * * * *